United States Patent [19]

Sandhaus

[11] Patent Number: 4,966,553
[45] Date of Patent: Oct. 30, 1990

[54] SET OF ATTACHMENT ELEMENTS FOR DENTAL PROSTHESES

[75] Inventor: Sami Sandhaus, Ecublens, Switzerland

[73] Assignee: Pharma Diffusion S.A., Switzerland

[21] Appl. No.: 339,160

[22] Filed: Apr. 17, 1989

[30] Foreign Application Priority Data

Apr. 27, 1988 [EP] European Pat. Off. ........ 88810272.0

[51] Int. Cl.⁵ ............................................. A61C 13/22
[52] U.S. Cl. ..................................... 433/181; 433/182
[58] Field of Search ................. 433/180, 181, 182, 183

[56] References Cited

U.S. PATENT DOCUMENTS 1,297,561  3/1919  Guntner ............................. 433/181
4,573,923  3/1986  Poveromo .......................... 433/181

FOREIGN PATENT DOCUMENTS 3444165  6/1986  Fed. Rep. of Germany ...... 433/182

Primary Examiner—Cary E. Stone
Attorney, Agent, or Firm—Anthony J. Casella; Gerald E. Hespos

[57] ABSTRACT

The set comprises:
at least one prismatic calcinable post (1) intended to be fastened to a crown and having at its base a support arm (2) and a cylindrical socket (3) arranged at the end of the support arm in a position parallel to the post,
calcinable connecting parts (19) intended to be integrated in the prosthesis,
fastening members (11, 12) for fastening the connecting parts on the prismatic post.

The post (1) and its socket (3) in offset position constitute an extracoronary universal socket element which is easily adjustable, combined with the modular nature of the connecting parts of the set permit the mounting of several types of different attachments with a minimum number of units attachable on one and the same post.

2 Claims, 1 Drawing Sheet

SET OF ATTACHMENT ELEMENTS FOR DENTAL PROSTHESES

The object of the present invention is a set of attachment elements for dental prostheses, comprising at least one calcinable prismatic post intended to be fastened to a crown and having a socket, and calcinable connecting pieces intended to be fastened to the socket and to form a support for a prosthesis.

The sets of attachment elements available on the market the calcinable elements of which are intended to disappear by calcining upon the molding of the prostheses, are all unifunctional, that is to say they always have a predetermined shape intended for a specific function, with the result that they cannot be adapted to the configuration of the dentition of the patient without a change in form, which requires adaptation, resulting in extensive work on the material and particularly o the dentition.

For this reason, the dental practitioner must preferably have on hand a large number of sets of attachment elements from which he may choose, depending on his requirements, that one which will require the least amount of adaptation and will best respect the integrity of the dentition of the patient. Such a choice is not always obvious.

The large number of sets of attachment elements offered on the market is clear proof of this need.

The object of the invention is to simplify the work of the dental practitioner by offering the best intrinsic adaptation of the material to the dental morphology of the patients, requiring only a minimum amount of retouch work solely on the material so as to permit a solution of most of the problems which arise in prosthetics.

For this purpose, a set of attachment elements of the invention, which is of the type defined at the beginning hereof, is characterized by a prismatic post having at its base a lateral support arm and a cylindrical socket arranged at the end of the support arm and spaced from the prismatic post, parallel to the latter and provided with an axial cylindrical hole, by connecting pieces which differ from each other and are interchangeable, each of them being adapted to a specific prosthesis, and by means for fastening the connecting pieces to the cylindrical socket of the post, each of them being adapted to a specific attachment.

In this way, the cylindrical socket, which is offset with respect to the prismatic post, becomes a universal socket element which can be used either as is without retouch work, or with retouchings in shapes which are easy to carry out due to its extra-coronary position in accordance with the shape and the nature of the connecting pieces intended to be attached thereto. The cylindrical shape of the socket combined with its cylindrical axial hole offers, in fact, a large number of possibilities for simple attachment of the connecting pieces by threading, forced fitting or internal or external clamping, depending on the permanent or removable nature of the prosthesis to be attached, and requiring only minimum retouch work such as tapping or boring of the cylindrical hole and radial cutting o axial milling of the cylinder.

This offset position of the cylindrical socket with respect to the prismatic post permits easy adaptation to the morphology of the patient by adjustment of the lower part of the post and of the support arm to the gum and by adjustment of its height by simple grindings.

In case of use for the attachment of a bridge, easy re-establishing of parallelism of convergent or divergent posts can be effected by simple correction by grinding of the face for the attachment of the posts on the crown, without requiring retouching of the teeth themselves.

Finally, together with the versatility of the cylindrical socket of the prismatic post, the different connecting parts and their fastening members, each adapted to a specific prosthesis and specific attachment, permit rationalization of the work of the dental practitioner bases on a minimum number of interchangeable parts which can be fastened to the same basic post.

The invention also has as object, based on its concept, a noncalcinable attachment element for dental prostheses, characterized by the fact that it is obtained by molding a calcinable attachment element coming from a set of attachment elements comprising at least one calcinable prismatic post, having at its base a lateral support arm and a cylindrical socket arranged at the end of the support arm and spaced from the prismatic post, parallel to the latter and pierced by an axial cylindrical hole, and also comprising calcinable connecting parts intended to be fastened to a dental prosthesis which differ from each other and are interchangeable, each of them being adapted to a specific prosthesis and comprising means for fastening the connecting parts to the cylindrical socket of the post, each adapted to a specific attachment.

Within the scope of the invention it may in fact be of interest for the dental practitioner to have noncalcinable elements which can be used directly for the attachment of a prosthesis, in particular, in the case of the intrinsic possibility of the adaptation of these elements to the morphology of the patient not requiring any adjustment retouches.

The invention will be better understood from the accompanying drawing and the description which follows.

The accompanying drawing shows, by way of example, one embodiment of the set of attachment elements forming the object of the invention.

Figure 1:
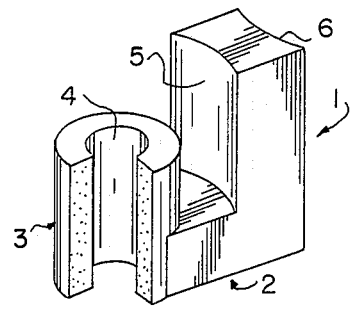
FIG. 1 is a perspective view of the basic element of this set.

The base element shown in FIG. 1, which is of a calcinable nature, is formed of a prismatic post 1 intended to be fastened on a dental crown, comprising at its base a support arm 2 of rectangular section forming an L with the post 1, and a cylindrical socket 3 arranged at the end of the support arm 2, spaced from the post 1 and parallel to it, pierced by a continuous axial cylindrical hole 4.

The prismatic post 1 has a first concave side surface 5 facing the cylindrical socket 3, the radius of curvature of which is centered on the axis of revolution of the socket, and a second concave lateral face 6 opposite the first, the radius of curvature of which corresponds to the average curvature of the side face of the customary crowns on which this post is intended to be fixed.

The concavity of the lateral face 5 permits the minimum distance between the axis of revolution of the cylindrical socket 3 and the post 1, taking into account the thickness of the lateral wall of the socket 3 and the thickness of the lateral wall of certain sleeve-shaped connecting parts intended to be fitted around said socket and which are described further below.

The concavity of the opposite face facilitates the adjustment of the post on the crown.

When these effects are not directly sought, the prismatic post 1 may be of rectangular cross section.

Figure 2:
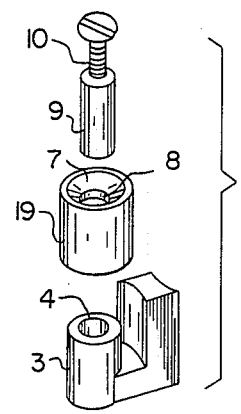

The first attachment structure shown, FIG. 2, which can be used for the attachment of a removable bridge, results from the mounting of a calcinable cylindrical sleeve 19 on the cylindrical socket 3 of the base element shown in FIG. 1 and from the inclusion in said socket of a cylindrical bushing 9 and its screw 10.

The cylindrical sleeve 19 has a frustoconical end 7 pierced by an axial hole 8 and has an inside diameter which corresponds to the outside diameter of the cylindrical socket 3 of the base element. This cylindrical sleeve is intended here to be pushed around the said cylindrical socket 3.

The cylindrical bushing 9 is pierced by an axial hole into which the screw 10 is intended to be screwed, this bushing being itself intended to be engaged in the axial hole 4 of the cylindrical socket 3, after the boring of this hole to the diameter of this bushing, through the axial hole of the cylindrical sleeve 19.

In a simplified variant (not shown) which is applicable to fixed prostheses, the attachment can be effected by direct screwing into the cylindrical socket 3 by means of a screw which forms part of the set, after prior tapping of the axial hole 4 of this cylindrical socket 3.

Figure 3:
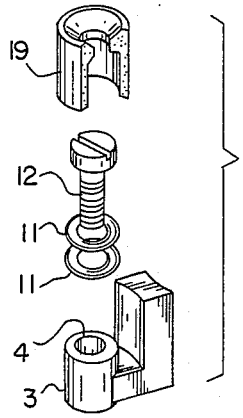

The second attachment structure shown, FIG. 3, can advantageously be applied to prostheses which require an attachment with elastic suspension. This second attachment structure results from the mounting of the calcinable cylindrical sleeve 19 which has been already described onto an elastic support composed of two elastic washers 11, which can be expanded laterally by axial pressure, of the type known in mechanical construction under the name of "0-ring", and a flat headed screw 12 passed through these two washers and threaded into the previously tapped axial hole 4 of the cylindrical socket 3 of the base element.

In this second attachment structure, the holding force of the cylindrical sleeve 19, after casting, can be modulated by means of the screw 12, and this is a particularly important advantage for this type of elastic suspension attachment.

The number of elastic washers 11 may be greater than 2, or else these washers of 0-ring type may be replaced by a single cylindrical washer formed, for instance, of a lenght of tube of elastic material.

Figure 4:
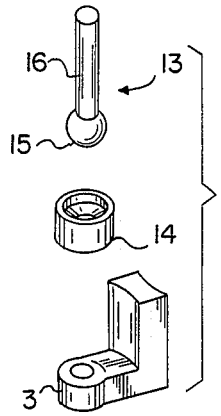

The third attachment structure shown, FIG. 4, can be used for prostheses which require an attachment which is not elastic but is capable of granting a certain freedom of angular displacement of small amplitude.

This third attachment structure results from the mounting of two calcinable male and female snap fasteners 13 and 14 on the previously radially cut cylindrical socket 3 of the base element.

The female snap fastener 14 is in the form of a cup with a flat bottom intended to be bonded onto the cut face of the cylindrical socket 3, and the cylindrical side wall of which has a inner peripheral retaining necking.

The male snap fastener 13 is in the shape of a spherical head 15 extended by a cylindrical rod 16, the spherical head 15 being intended to be partially imprisoned by forced clipping into the cup of the female snap fastner 14. The cylindrical rod 16 of this male snap fastener 13 is of a diameter capable of permitting its force-fitting in the hole 4 of the cylindrical socket 3 of the base element for use in another attachment structure, described below.

In a variant (not shown) of the female snap fastener 14, it also has a cylindrical axial rod intended for its attachment on the socket 3 of the base element by the force-fitting of said rod in the axial hole 4 of said socket.

Figure 5:
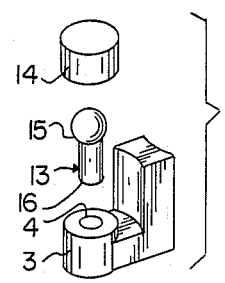
FIGS. 2, 3, 4, 5 and 6 are exploded views in pespective of five different attachment structures, each resulting from the assembling of certain calcinable connecting parts of this set to the base element shown in FIG. 1.

The fourth attachment structure shown, FIG. 5, is for the same application as the preceding one and is composed of the same calcinable elements, with the difference that here the connection is inverted, the male snap fastener 13 being force-fitted by its cylindrical rod 16 in the hole 4 of the cylindrical socket 3 of the base element and the female snap fastener 14 being forcefully clipped over the spherical head 15 of the male snap fastener 13.

Figure 6:
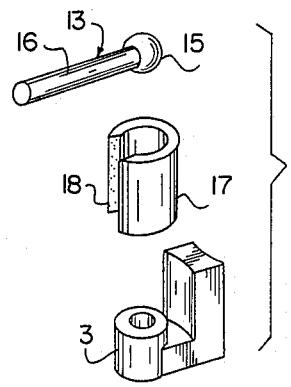

The fifth and last attachment shown, FIG. 6, is comparable in its application to the third structure, shown in FIG. 4, with the difference that the connecting part is formed by a bottomless cylindrical sleeve 17 the side wall of which has an axial slot 18 over its entire height, this sleeve being intended to be fastened by pushing it around the cylindrical socket 3 of the base element.

Depending on the lenght given to this sleeve 17, one or more male snap fasteners 13 of the type already described can be force fitted with their rod 16 in radial position of engagement in the slot 18.

In this embodiment of the set of attachment elements which has been given by way of example and is illustrated in the drawing, the modular nature of the connection conformations of the calcinable elements, such as those of the socket 3 of the base element and those of the sleeves 17 and 19 and of the snap fasteners 13 and 14 accounts to a great extent for the ability to rationalize the work of the dental practitioner which is provided by the invention.

However this embodiment is not limitative and changes may be made not only in its structural shapes, such as those already indicated previously, but also in its functional structures, which may either be provided in the design of the elements or established by the dental practitioner himself.

Thus, for instance, the cylindrical socket 3 of the base element can be bored to a diameter substantially less than that of the spherical head 15 of the male snap fastener 13 and its side wall can be slotted laterally, either over its entire height by a single slot or by several slots which are stopped at the bottom or upper level of the support arm 2. By this simple appropriation it is possible to engage one or more male snap fasteners 13 in this socket 3 and maintain them by greater or lesser elastic pressure.

Finally, since the calcinable elements of the invention are intended to be cast after mounting and adjustment of the attachment structures, the invention also extends to any noncalcinable element coming from the molding of any of its calcinable elements of origin. This due to the fact that it is to the interest of the dental practitioner to avoid casting when the structural shapes of the calcinable elements fit the morphology of the patient without retouch or almost without retouch.

I claim:

1. A set of attachment elements for dental prostheses comprising in combination:

a calcinable prismatic post having a base portion;

a calcinable lateral support arm connected to said base portion, transversely to the prismatic post;

a calcinable cylindrical socket having a longitudinal hole, said cylindrical socket being connected to said lateral support arm at a distance from said prismatic post and in parallel relationship therewith;

a first concave lateral face on said prismatic post, said first face being directed towards said cylindrical socket;

a second concave lateral face on said prismatic post, said second face being opposed to said first concave lateral face;

a plurality of interchangeable calcinable liaison means; and means for alternatively fastening said liaison means one at a time to said cylindrical socket.

2. A set of attachment elements for dental prostheses comprising in combination:

a calcinable prismatic post having a base portion;

a calcinable lateral support arm connected to said base portion, transversely to the prismatic post;

a calcinable cylindrical socket having a longitudinal hole, said cylindrical socket being connected to said lateral support arm at a distance from said prismatic post and in parallel relationship therewith;

a first concave lateral face on said prismatic post, said first face being directed towards said cylindrical socket;

a second concave lateral face on said prismatic post, said second face being opposed to said first concave lateral face;

a first interchangeable calcinable liaison means forming a cylindrical sleeve having a frustoconical bottom and a longitudinal hole adapted to fit around said cylindrical socket;

a second interchangeable calcinable liaison means forming a male snap fastener having a spherical head extended by a cylindrical rod adapted to force fit into the longitudinal hole of said cylindrical socket and a female snap fastener adapted to force clip onto the spherical head of said male snap fastener;

a third interchangeable calcinable liaison means forming a bottomless cylindrical sleeve adapted to force fit around said cylindrical socket and having a lateral wall and a longitudinal slot in said wall, and a male snap fastener having a spherical head adapted to be force fitted into said cylindrical sleeve and a cylindrical rod extending from said spherical head and adapted to be engaged into said longitudinal slot;

a first means for fastening said first liaison means to said cylindrical socket comprising a cylindrical bushing having a longitudinal threaded hole and a screw for threading into said threaded hole, said cylindrical bushing being adapted to be engaged into the longitudinal hole of said cylindrical socket and through the longitudinal hole of said first liaison means; and a second means for alternatively fastening said first liaison means to said cylindrical socket comprising at least one elastic washer and a screw adapted to pass through said washer and thread into the longitudinal hole of said cylindrical socket, said elastic washer being adapted to elastically force fit into the longitudinal hole of said first liaison means.

* * * * *